United States Patent [19]

Spector

[11] Patent Number: 4,707,338

[45] Date of Patent: * Nov. 17, 1987

[54] LIGHT-ACTIVATED AROMA GENERATOR WITH AUTOMATIC CUTOFF

[76] Inventor: Donald Spector, 380 Mountain Rd., Union City, N.J. 07087

[*] Notice: The portion of the term of this patent subsequent to Sep. 22, 2004 has been disclaimed.

[21] Appl. No.: 932,611

[22] Filed: Nov. 20, 1986

Related U.S. Application Data

[63] Continuation-in-part of Ser. No. 765,152, Aug. 13, 1985, which is a continuation-in-part of Ser. No. 592,915, Mar. 23, 1984, Pat. No. 4,568,521.

[51] Int. Cl.$^4$ .............................................. A61L 9/17
[52] U.S. Cl. ..................................... 422/124; 239/54; 361/173; 362/96; 422/4; 422/5; 422/105
[58] Field of Search ................ 422/105, 4, 5, 124, 422/123; 361/173-175; 362/96, 101; 239/54, 55

[56] References Cited

U.S. PATENT DOCUMENTS

| | | | |
|---|---|---|---|
| 1,957,509 | 5/1934 | Vallen | 361/175 |
| 2,614,820 | 10/1952 | Baydjieff | 422/5 |
| 2,986,689 | 5/1961 | Hofer | 361/133 |
| 3,609,450 | 9/1971 | Hart | 250/215 |
| 4,242,831 | 1/1981 | O'Shaughnessy | 361/175 |
| 4,301,095 | 11/1981 | Mettler et al. | 422/124 |

Primary Examiner—Barry S. Richman
Assistant Examiner—William R. Johnson
Attorney, Agent, or Firm—Michael Ebert

[57] ABSTRACT

An aroma generator that is rendered operative only when a switch-controlled electric light bulb is in a predetermined state which is either "on" or "off," the generator then functioning to discharge an air current conveying an aromatic vapor which modifies the prevailing atmosphere. Included in the generator is a motor-driven fan that forces air through an air-permeable cartridge containing an aroma supply. The motor is connected to a battery through a signal-responsive electronic relay having time delay means such that when the relay is activated by a signal to turn on the fan, it is thereafter automatically deactivated after a predetermined time period. Applied to the relay is a binary signal derived from a light sensor adjacent the light bulb to intercept light rays therefrom, the signal being positive when the bulb is switched "on" and negative when it is switched "off." In one embodiment, the relay responds only to a positive signal, in which event the aroma generator is rendered operative for a predetermined period when the bulb is switched "on." In another embodiment, the relay responds only to a negative signal, in which event the aroma generator is rendered operative for a predetermined period when the bulb is switched "off."

7 Claims, 4 Drawing Figures

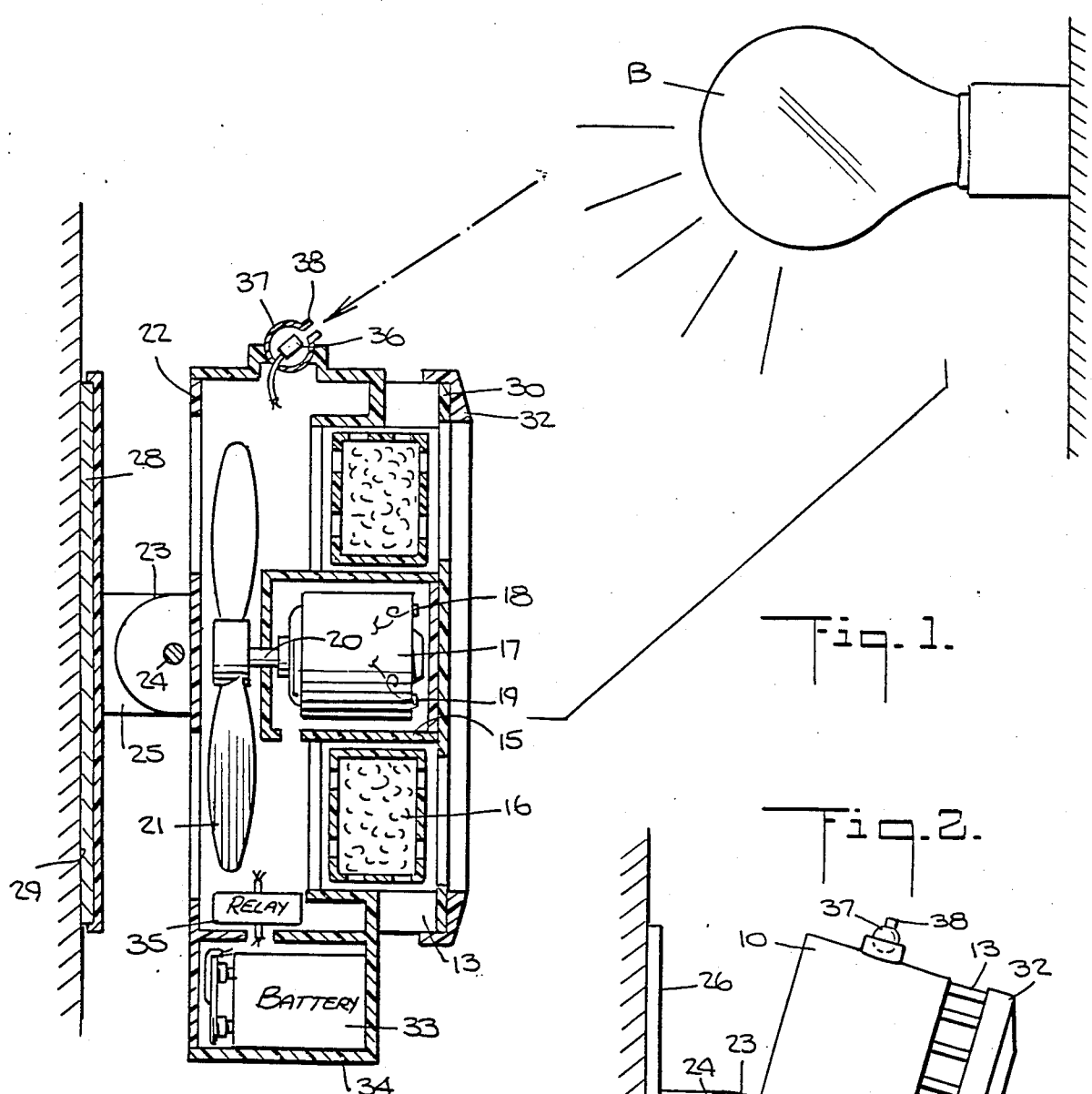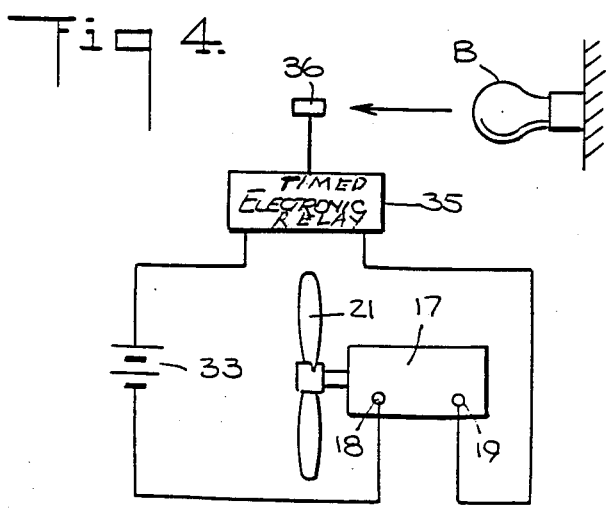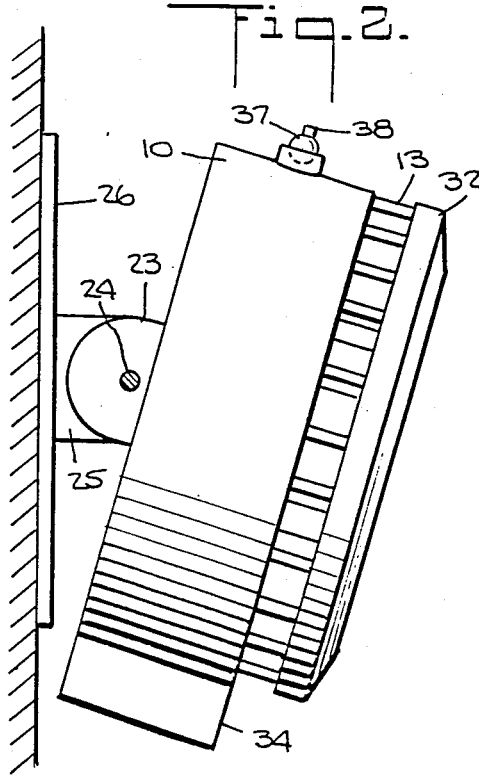

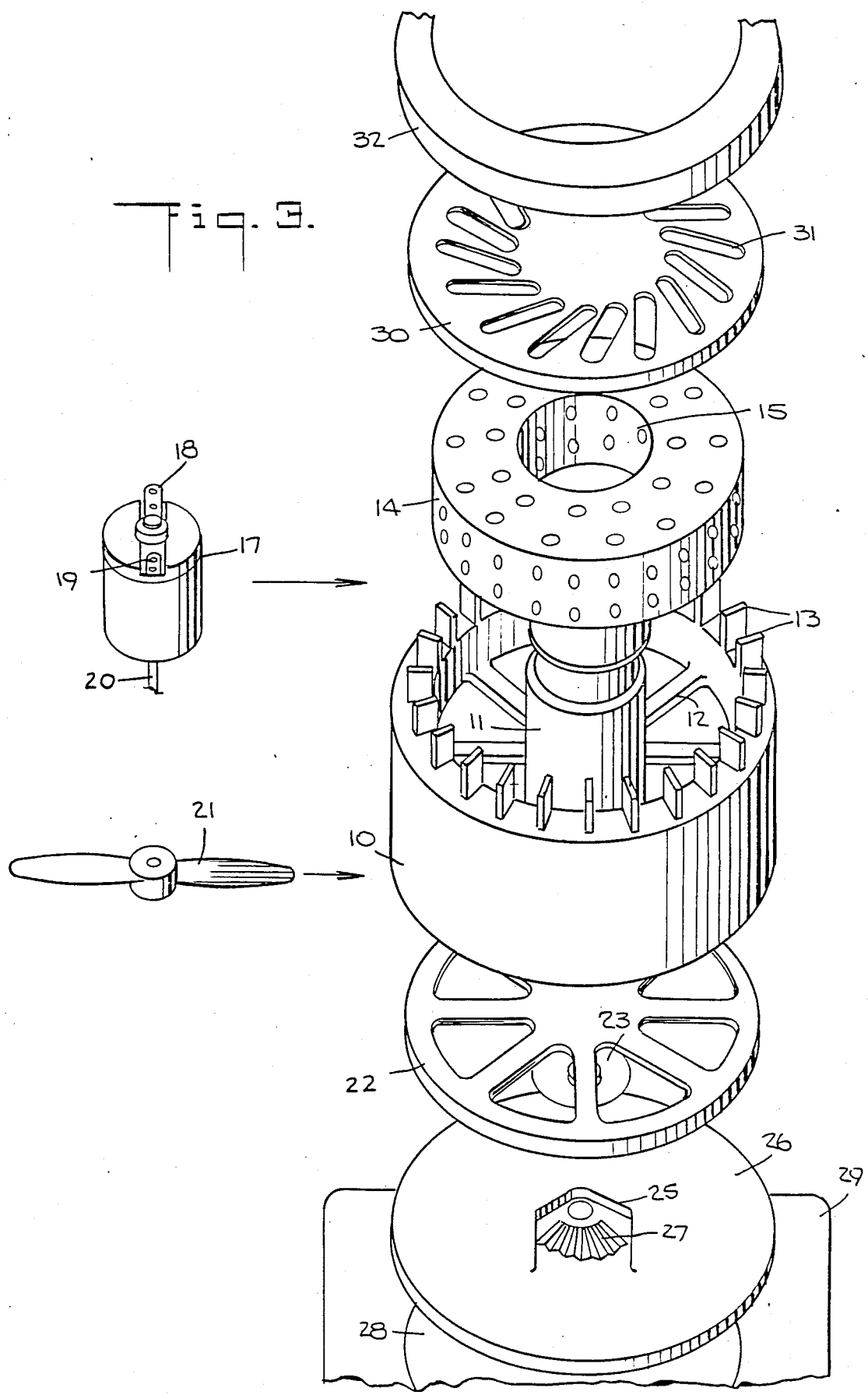

LIGHT-ACTIVATED AROMA GENERATOR WITH AUTOMATIC CUTOFF

RELATED APPLICATIONS

This application is a continuation-in-part of my copending application Ser. No. 765,152, filed Aug. 13, 1985, which in turn is a continuation-in-part of my copending application Ser. No. 592,915, filed Mar. 23, 1984, now U.S. Pat. No. 4,568,521 issued Feb. 4, 1986, entitled "Solar Powered Aroma Generator," the entire disclosures of these earlier applications being incorporated herein by reference.

BACKGROUND OF INVENTION

Field of Invention

This invention relates generally to aroma generators, and more particularly to a fan-operated aroma generator that is automatically rendered operative for a predetermined period when a switch-controlled light bulb in the area in which the generator is installed is in a predeteremined state which is either "on" or "off," the generator being otherwise deactivated.

In order to modify the atmosphere of a room, it is known to discharge therein air fresheners, deodorizers or aromatic vapors which function to mask or supplant the prevailing odor and render it more agreeable. As used herein, the term "aroma" is generic to all such air modifiers; it is not limited to pleasing fragrances or perfumes, and encompasses various scents or odors that act in some way to modulate the atmosphere of a room.

Certain types of air fresheners are appropriate to heavily-used lavatories and bathrooms, or rooms whose atmosphere is contaminated by tobacco smoke or cooking odors. In other instances, as in bedrooms, a perfumed environment may be more suitable. Hence the effect sought when modifying an atmosphere depends on its initial state and the desired state.

To satisfy the requirements for improving or modifying the atmosphere to create a more agreeable environment, it is known, as in the patent to Koritz, U.S. Pat. No. 4,102,656, to blow air through a filter saturated with an aromatic liquid compound, use being made of a motor-driven fan for this purpose. Along similar lines, is the air purifier disclosed in the Madjar U.S. Pat. No. 4,078,891 in which a blower forces air through a filter impregnated with a disinfectant or perfume.

The above-identified patents make use of fan motors energized from a power line, whereas in the Corris U.S. Pat. No. 3,990,848 the fan which forces air through a porous cartridge containing a room deodorizer or germicide is battery-operated.

In order to activate the air purifier at different times and for different intervals, the above-identified Madjar patent provides a timed switch for this purpose. Also of interest is the patent to Boydjieff, U.S. Pat. No. 2,614,820, showing a portable vapor-projecting device for perfuming the air and including a timer switch to drive the fan motor for a preset interval. But the timing of this operation is preset and does not depend on unpredictable random actions. Thus, in the case of the typical bathroom, there is no way of knowing in advance when the bathroom will be occupied or for how long.

One could, of course, provide an aroma generator of the types disclosed in the above-noted patents with a conventional power switch, so that each time a person enters a room in which the generator is installed, he could turn on the generator, and before leaving the room he could switch it off.

There are, however, several drawbacks incident to the use of such conventional control switches. Thus, when a home bathroom is used by a guest, the guest may not know that an aroma generator is installed therein, particularly if the generator is so designed as to assume the appearance of an ornamental object rather than a utilitarian device.

But even if the guest or a resident in the home knows that an aroma generator is installed in the bathroom and turns it on when entering the room, he may thereafter forget to turn it off when leaving. Should the aroma generator then continue to operate, the accumulated amount of aroma then exuded into the atmosphere may be so great as to cause it to spill into adjacent areas or rooms where the bathroom aroma is altogether inappropriate. Moreover, continuous operation of the aroma generator will shorten the effective life of whatever cartridge or pad is used as the aroma supply.

A more serious drawback of aroma generators which derive their power from a high-voltage power line and therefore have to be plugged into the line, is that such devices present a possible electrical hazard in a bathroom where water in some form is inevitably present, and where an individual standing on a wet floor or in a tub, should he then touch the aroma generator, may receive an electrical shock. It is for this reason that battery-operated aroma generators are preferably for bathroom environments.

In my above-identified copending application Ser. No. 765,152, there is disclosed an aroma generator that is automatically activated when one switches on an electric light bulb in the room in which the generator is installed, the generator then functioning to discharge an air current into the room conveying an aromatic vapor which modifies the prevailing atmosphere.

Included in the generator is a motor-driven fan that forces air through an air permeable cartridge containing an aroma supply, the motor being connected to a battery through a signal-responsive electronic relay. Applied to the relay is a signal derived from a light sensor which is adjacent the light source to intercept light rays therefrom. The arrangement is such that when the bulb is switched "on," the resultant signal from the sensor is then of sufficient magnitude to actuate the relay and thereby render the generator operative, whereby the operation of the aroma generator is coordinated with that of the bulb without any wire connection therebetween.

The practical difficulty with the battery-powered aroma generator disclosed in my copending application Ser. No. 765,152 is that it is subject to misuse resulting in a shortened battery life. If, for example, the battery-powered aroma generator is installed in a bathroom next ao a switch-controlled light bulb, the generator will normally be operative only during the relaively short period in which the bathroom is occupied and the light is turned "on." But while it is wasteful to leave the light on when leaving a bathroom, in many cases the light is not switched off; hence the aroma generator continues to operate for a prolonged period or even indefinitely until the batteries are exhausted.

And in such prolonged operation, the fragrance cartridge which exudes an aroma at a relatively high rate when the motor-driven fan is operative, continues to do so even though there is no need for an aroma discharge when the bathroom is no longer occupied. Hence the fragrance cartridge is also prematurely exhausted.

SUMMARY OF INVENTION

In view of the foregoing, the main object of this invention is to provide an aroma generator having a battery-powered fan motor that is automatically rendered operative for a predetermined period when an electric light source disposed at a position adjacent the generator is switched "on," the generator being automatically activated at the conclusion of the period even though the light source is still switched "on."

More particularly, an object of the invention is to provide an aroma generator of the above type which includes a light sensor which controls the operation of the battery-powered motor, the light sensor being adapted to intercept light from the bulb or other light source to produce a binary signal which is positive when the source is switched "on" and negative or zero when the source is switched "off."

Also an object of the invention is to provide an air-permeable cartridge filled with fragrance beads which exude an aroma at a relatively high rate when an air current is blown therethrough by the fan and which continues to exude an aroma at a much lower rate when the fan is deactivated whereby the aroma generator maintains a low level of aroma in the room or chamber in which the generator is installed.

Also an object of the invention is to provide a cartridge type aroma generator in which the cartridge, when exhausted may readily be replaced by a fresh cartridge yielding the same or a different aroma.

Still another object of the invention is to provide an aroma generator which is automatically rendered operative for a predetermined time period when an electric light source disposed at a fixed position adjacent the generator is switched "off," the generator being automatically de-activated at the conclusion of the time period even though the light source is still switched "off." Thus, the generator may be installed in a refrigerator or a closet having a light bulb therein to illuminate the interior. The door of the refrigerator or closet cooperates with a pin-switch which controls the operation of the bulb, such that when the door is closed, this acts to turn the light "off."

A significant advantage of the invention is that it acts not only to conserve battery power, but it also extends the effective life of the aroma cartridge.

Briefly stated, these objects are attained in an aroma generator that is rendered operative only when a switch-controlled electric light bulb is in a predetermined state which is either "on" or "off," the generator then functioning to discharge an air current conveying an aromatic vapor which modifies the prevailing atmosphere. Included in the generator is a motor-driven fan that forces air through an air-permeable cartridge containing an aroma supply. The motor is connected to a battery through a signal-responsive electronic relay having time delay means such that when the relay is activated by a signal to turn on the fan, it is thereafter automatically deactivated after a predetermined time period. Applied to the relay is a binary signal derived from a light sensor adjacent the light bulb to intercept light rays therefrom, the signal being positive when the bulb is switched "on" and negative when it is switched "off." In one embodiment, the relay responds only to a positive signal, in which event the aroma generator is rendered operative for a predetermined period when the bulb is switched "on." In another embodiment, the relay responds only to a negative signal, in which event the aroma generator is rendered operative for a predetermined period when the bulb is switched "off."

OUTLINE OF DRAWINGS

For a better understanding of the invention as well as other objects and further features thereof, reference is made to the following detailed description to be read in conjunction with the accompanying drawings, wherein:

FIG. 1 is a sectional view of an aroma generator in accordance with the invention;

FIG. 2 is a side view of the aroma generator when mounted on a wall;

FIG. 3 is an exploded view of the aroma generator; and

FIG. 4 is a schematic diagram of the generator.

DESCRIPTION OF INVENTION

First Embodiment

Referring now to FIGS. 1, 2 and 3, an aroma generator in accordance with the invention includes a cylindrical case 10 having a tubular socket 11 supported coaxially therein by a spider 12. Projecting from the front edge of the case is a circular array of fins 13. This structure and all other components are preferably molded from synthetic plastic material having good physical properties, such as polypropylene, polyvinyl chloride or ABS.

Seated on spider 12 within case 10 is a replaceable fragrance cartridge 14 having a circular center hole 15 through which socket 11 extends. The cartridge walls are foraminated so that the cartridge is permeable to air. The cartridge is filled with a charge of fragrance beads 16 of the type commonly used in commercial air fresheners, the fragrance being exuded from the beads at a rate determined by air flow through the air-permeable cartridge. Thus, in the absence of forced air flow, the rate of exudation is relatively slow and the cartridge has an extended effective life.

The invention is not limited to fragrance beads, for any aromatic supply may be used in the cartridge, such as a porous pad impregnated with a liquid fragrance. Nor is the invention limited to any particular aroma, and use may be made of deodorizers, air fresheners, perfumes or any other atmosphere-modifying agent.

Received within tubular socket 11 is a miniature low-voltage direct-current motor 17 in cylindrical form having a pair of terminals 18 and 19 at one end and a central shaft 20 projecting from the other end. Supported on this shaft is a propeller fan 21 which rotates within the rear end of body 10 behind spider 12, the back being closed by a closure plate 22 having a spoked wheel formation.

Closure plate 22 is provided at its rear with a semicircular tab 23 which projects from the hub of the plate. Tab 23 is attached by a pivot pin 24 to a stud 25 projecting from the front face of a mounting disc 26. One side of stud 25 is provided with a radial array of ridges 27 which frictionally engage the corresponding side of swivel tab 23 to resist displacement of the swivel.

The rear face of mounting disc 26 has attached thereto a layer 28 of pressure-sensitive adhesive material, making it possible to mount the generator at any desired site on a wall 29 adjacent a light bulb B which in practice may be any light bulb in a bathroom or other facility. Because of the swivel, the generator may be oriented relative to the wall to optimize its effectiveness. Thus, if the generator is mounted at an elevated position on the wall, it may then be tilted down to direct the aroma toward the occupants of the room.

The front face of cartridge 14 is covered by a disc 30 having an array of vents 31 therein. This disc is held in place by a cover ring 32 which engages the upper portions of fins 13 on the main body 10, the lower portions being exposed to permit aromatic vapors to be discharged omnidirectionally from the circular periphery of the cartridge.

The terminals 18 and 19 of motor 17 are connected to a battery 33 which is housed in a compartment 34 integral with case 10, the connection between the battery and the motor being in series with a signal-responsive solid state electronic relay 35 disposed within the case, so that the motor is powered only when the relay is activated. The relay circuit includes a resistance-capacitance time delay network or similar timing means which acts after a predetermined time interval determined by the timing characteristics of the network to automatically deactivate the relay at the conclusion of the period.

Applied to relay 35 is a binary signal derived from a light sensor 36 which is disposed within an orientable ball joint 37 on the side of the casing, so that the sensor may be oriented to pick up light rays from bulb B regardless of where it is mounted on the wall relative to the bulb.

The electronic relay 35 may be any solid state switching device such as a transistor circuit which is rendered conductive when a signal pulse is applied to its control or gate element exceeding a threshold level, the circuit then being latched to maintain the transistor activated and being unlatched at the conclusion of the timed period. Various types of such electronic relays are disclosed in Section 15 of the *Electronics Engineers' Handbook*, D.G. Fink, McGraw-Hill Book Co., first edition.

The light sensor 36 may be a photovoltaic sensor such as a selenium or silicon cell which generates a binary signal as a function of the illumination incident thereto, or it may be in the form of a photoconductive function semi-conductor or photo-transistor. By "binary signal" is meant that the signal is positive when the sensor is irradiated by light rays from the bulb, and is negative or zero when the bulb is switched "off." Regardless of the type of light sensor used, its relationship to the electronic relay in this embodiment is such that the relay is activated only when the light incident to the sensor is at an intensity well above that of ambient natural light in the room to produce a positive signal.

Thus, while there may be ambient natural light in the room which will result in some signal output from the light sensor, the relationship is such that this output is insufficient to actuate the electronic relay and power the motor. As a consequence, when the light bulb or other light source such as a fluorescent lamp is turned off, the generator exudes only a low level of aroma, for the fan is not then operative and no air is then forced through the cartridge. This low level in the static condition of the generator acts to prime the atmosphere of the room, but little aroma seepage from the room takes place even if the door is open; for the fragrance in the atmosphere is diluted. But when one enters the room and turns on the light, then the motor is automatically energized and the fan drives a current of air through the cartridge, which current is discharged into the atmosphere and carries with it an aromatic vapor to step up the fragrance in the room to a high level. At the conclusion of the timing period, the relay is deactivated and the discharge is discontinued even though the bulb is still "on."

Thus, the electronic relay is so arranged, that when the bulb to which the sensor is exposed is first switched "on" the resultant signal pulse from the sensor is positive, and this positive pulse acts to gate the relay which remains activated until it is deactivated by the timing circuit, say, 15 or 30 seconds later. This period must be long enough to suffuse the room with an aroma having sufficient lasting power to modify the room atmosphere for, say, 20 minutes.

The timed electronic relay may be of the type included in commercially-available miniature electronic calculators and other battery-operated units provided with an automatic cutoff circuit to deactivate the unit should it not be in operating use for a predetermined period, thereby conserving battery power. In the present situation, the relay not only conserves battery power, but it also prolongs the effective life of the aroma cartridge.

Second Embodiment

In another embodiment of the invention, the aroma generator may be used in a chamber in a situation where it is desirable to discharge a deodorant, an air freshener, an insecticide or other aroma appropriate to the environment when the door to the chamber is closed.

Thus, the typical refrigerator is provided with a light bulb to illuminate its interior. The light bulb is operated by a pin-switch cooperating with the refrigerator door so that when the door is open, the bulb is turned "on" to illuminate the interior, the bulb being turned "off" when the door is closed. In this situation, it is desirable to discharge into the interior an air freshener of a type acting to prevent food products in the interior from acquiring an unpleasant taste or disagreeable odor. To this end, the aroma generator is so placed in the refrigerator interior that its sensor is then adjacent the light bulb therein, and its electronic relay circuit is arranged to be responsive to a negative signal pulse from the sensor; that is, a signal surge produced when the refrigerator door is shut and the bulb is abruptly turned off.

To this end, the negative signal is applied to the relay through an electronic inverter so that the relay is activated for a predetermined period when a negative signal pulse is applied to the inverter input whose output is then positive to activate the relay. When, however, the sensor binary signal pulse is positive as a result of the door being open and the light being "on," the sensor signal is then positive and is inverted to be negative, so that it does not then activate the relay.

Similarly, in a clothing closet having a light bulb therein which is turned "on" by a pin switch when the closet door is opened to illuminate the interior of the closet, one may place the aroma generator adjacent the light bulb so that its sensor is exposed to light from the bulb, in which case the generator is activated only at the instant the door is closed and the light turned "off." The aroma generator then discharges for a predetermined period an insecticide effective against moths and other insects which are destructive of clothing. The generator is not again activated until the door is thereafter opened and again shut. In this instance, the beads in the aroma cartridge may be constituted by miniature moth balls.

When the aroma generator is intended for use in a closet or refrigerator, it need not be adhesively mounted on a wall adjacent the light bulb, but simply rested on a shelf. Hence for this purpose the case of the aroma generator may be in a box-like format rather than cylindrical as shown.

While there have been shown and described preferred embodiments of a light-activated aroma generator with automatic cutoff in accordance with the invention, it will be appreciated that many changes and modification may be made therein without, however, departing from the essential spirit thereof.

I claim:

1. In combination with a switch-controlled light bulb disposed in a chamber, an aroma generator which is rendered operative to modify the atmosphere of the chamber only when the switch connected to the light bulb is operated to put the bulb in an "on" or an "off" state, said generator comprising:
   A. a case disposed at a position adjacent the bulb and including a compartment for housing of a battery;
   B. a low-voltage direct-current motor coupled to a propeller fan and which is housed in said case;
   C. a light sensor mounted on said case to intercept light rays from said light source to produce a binary signal pulse when the switch is operated, the polarity of the pulse being positive in said "on" state and negative in the "off" state;
   D. an air-permeable cartridge containing an aroma supply and disposed in said case in operative relation to said fan to exude an aroma into the atmosphere of the chamber at a relatively rapid rate only when an air current is forced through said cartridge by said fan; and
   E. signal responsive electronic relay coupled to said sensor and activated by a signal pulse of a given polarity, to connect said battery to said motor to render the generator operative, said relay including a time delay which automatically deactivates the relay after a predetermined period whereby the generator is cut off at the conclusion of the period and is not again rendered operative until the switch is again operated to produced a signal pulse of said given polarity.

2. The combination as set forth in claim 1, wherein said relay is activated by a positive pulse signal whereby the generator is rendered operative when the switch is operated to turn the bulb "on."

3. The combination as set forth in claim 1, wherein said relay is activated by a negative pulse signal whereby the generator is rendered operative when the switch is operated to turn the bulb "off."

4. The combination as set forth in claim 1, further including adhesive means to mount said generator on a wall adjacent said bulb.

5. The combination as set forth in claim 1, wherein the aroma supply in said cartridge is constituted by a charge of fragrance beads.

6. The combination as set forth in claim 5, wherein the beads exude an air freshener aroma.

7. The combination as set forth in claim 5, wherein said beads are miniature moth balls.

* * * * *